(12) United States Patent
Jackson et al.

(10) Patent No.: US 6,475,148 B1
(45) Date of Patent: Nov. 5, 2002

(54) MEDICAL DIAGNOSTIC ULTRASOUND-AIDED DRUG DELIVERY SYSTEM AND METHOD

(75) Inventors: John I. Jackson, Menlo Park, CA (US); Edward A. Gardner, San Jose, CA (US)

(73) Assignee: Acuson Corporation, Mountain View, CA (US)

( * ) Notice: Subject to any disclaimer, the term of this patent is extended or adjusted under 35 U.S.C. 154(b) by 32 days.

(21) Appl. No.: 09/696,411

(22) Filed: Oct. 25, 2000

(51) Int. Cl.$^7$ ................................................. A61B 8/12
(52) U.S. Cl. .......................................... 600/439; 601/2
(58) Field of Search .................................. 600/437, 439, 600/440, 441, 443, 447, 454, 458; 601/2; 604/22, 290; 424/489, 491, 493

(56) References Cited

U.S. PATENT DOCUMENTS

| | | | |
|---|---|---|---|
| 5,158,071 A | | 10/1992 | Umemura et al. |
| 5,190,766 A | * | 3/1993 | Ishihara ........................ 424/489 |
| 5,267,985 A | * | 12/1993 | Shimada et al. ............. 604/290 |
| 5,325,860 A | | 7/1994 | Seward et al. |
| 5,345,940 A | | 9/1994 | Seward et al. |
| 5,435,311 A | | 7/1995 | Umemura et al. |
| 5,542,935 A | | 8/1996 | Unger et al. |
| 5,581,517 A | | 12/1996 | Gee et al. |
| 5,675,554 A | | 10/1997 | Cole et al. |
| 5,823,962 A | | 10/1998 | Schaetzle et al. |
| 6,077,225 A | * | 6/2000 | Brock-Fisher ............... 600/439 |
| 6,131,458 A | * | 10/2000 | Langdon et al. ............. 600/443 |

OTHER PUBLICATIONS

Ralph V. Shohet, M.D. et al.—"Echocardiographic Destruction of Albumin Microbubbles Directs Gene Delivery to the Myocardium", Dept. of Internal Medicine, University of Southern Texas, Southwestern Medical Center, Circulation Jun. 2, 2000, pp. 2554–2556.

Sanjiv Kaul, M.D.—"Myocadial Contrast Echocardiography—15 Years of Research and Development", Cardiovascular Division, University of Virginia School of Medicine, Circulation 1997, pp. 3745–3760.

Peter J. A. Frinking et al.—"Effect of Ultrasound On The Release of Micro–Encapsulated Drugs", Ultrasonics 36, 1998, pp. 709–712.

Press Release—"Ultrasound–Enhanced Drug Delivery", from newswire at Acuson on Oct. 6, 1998, from ccMail by smtgate.acuson.com.

* cited by examiner

*Primary Examiner*—Marvin M. Lateef
*Assistant Examiner*—Ali M. Imam

(57) ABSTRACT

A method and system is provided for delivering drugs carried by microspheres. A medical diagnostic ultrasound system destroys microspheres in a specific localized area or at a specific time. A region of interest that is a subset of an imaged area is identified for destroying drug-carrying microspheres. The transmit beamformer is configured to transmit acoustic energy for destroying microspheres within that area while minimizing the destruction of microspheres outside of the region of interest. A multidimensional transducer array may provide focusing in three-dimensions for accurately destroying microspheres in the specific region while minimizing the destruction of microspheres outside that region. A trigger responsive to a heart or breathing cycle may control when microspheres are destroyed, providing delivery of drugs at the most opportune time in the cycle.

38 Claims, 2 Drawing Sheets

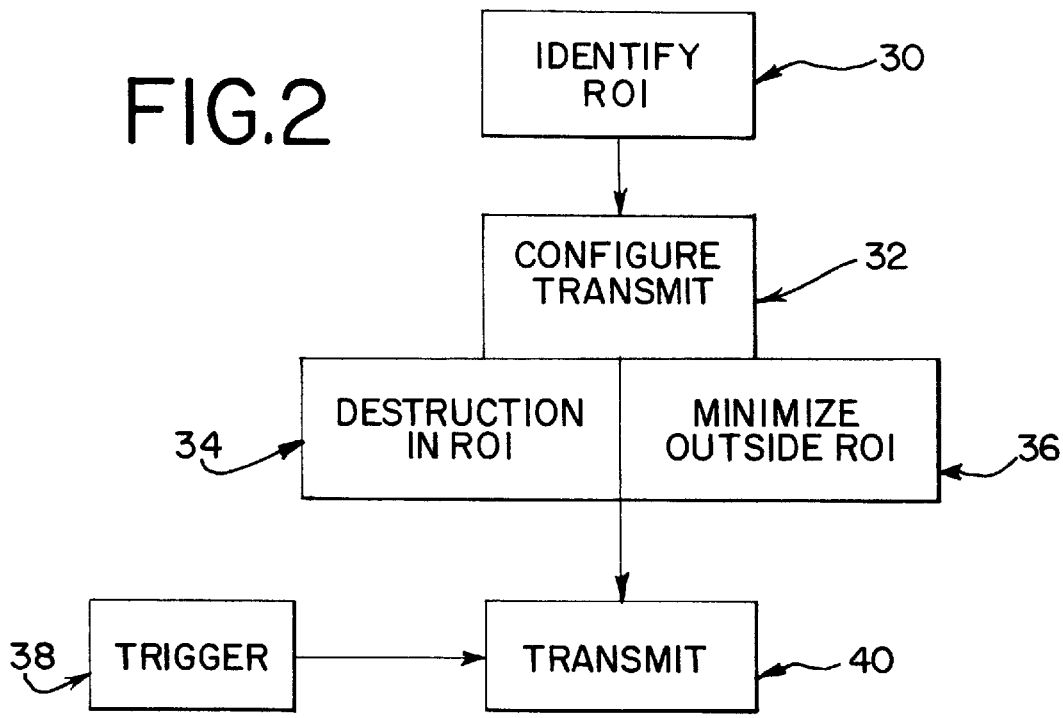
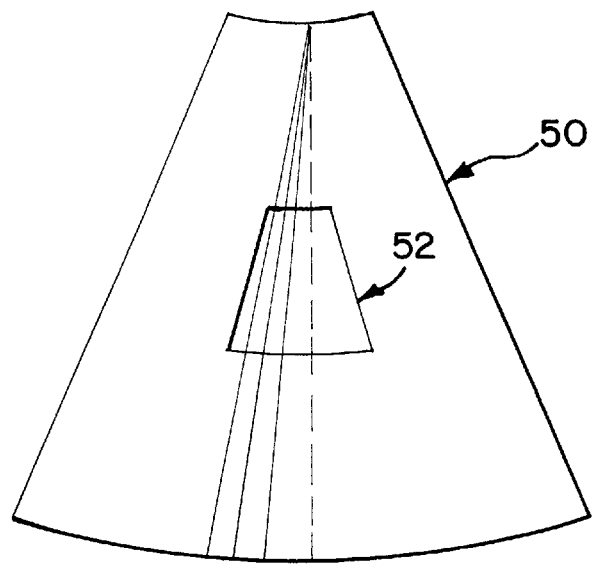

MEDICAL DIAGNOSTIC ULTRASOUND-AIDED DRUG DELIVERY SYSTEM AND METHOD

BACKGROUND

The present invention relates generally to using ultrasound for delivery of drugs from microspheres. Diagnostic medical ultrasound imaging has been used to image microspheres. The microspheres are imaged using linear, nonlinear or stochastic responses of the microspheres to varying intensities of acoustic pressure. In addition to imaging microspheres, medical diagnostic ultrasound systems destroy microspheres with acoustic energy. The destruction of the microspheres is optimized such that subsequent imaging shows an inflow or wash-in of new microspheres into the image region or provides a loss of correlation.

The destruction of microspheres may provide more efficient delivery of drugs. In "Echocardiographic Destruction Of Albumin Directs Gene Delivery To The Myocardium", Circulation, June 2,000, R. Shohet, Paul Grayburn and others delivered an adenoviral transgene to a rat myocardium using ultrasound medicated microbubble destruction. The microspheres used comprised albumin coated microbubbles. A tenfold increase in activity of the drug was produced.

BRIEF SUMMARY

The present invention is defined by the following claims, and nothing in this section should be taken as a limitation on those claims. By way of introduction, the preferred embodiment described below includes a method and system for delivering drugs carried by microspheres. A medical diagnostic ultrasound system is used to destroy microspheres, releasing drugs in a specific localized area or at a specific time.

In one aspect, a region of interest that is a subset of an imaged area is identified for destroying drug-carrying microspheres. The transmit beamformer is configured to transmit acoustic energy for destroying microspheres within that area while minimizing the destruction of microspheres outside of the region of interest. In a second aspect, a multidimensional transducer array provides elevation focusing for accurately destroying microspheres in a specific region while minimizing the destruction of microspheres outside that region. In a third aspect, a trigger, such as a trigger responsive to a heart or breathing cycle, determines when microspheres are destroyed, providing delivery of drugs at the most opportune time in the cycle.

Other aspects and advantages of the invention are discussed below in conjunction with preferred embodiments.

BRIEF DESCRIPTION OF SEVERAL VIEWS OF THE DRAWINGS

FIG. 2 is a flow chart of one embodiment of a method for generating acoustic energy to deliver drugs from microspheres.

FIG. 3 is a graphical representation of one embodiment of an ultrasound image and associated region of interest for the destruction of microspheres.

DETAILED DESCRIPTION OF THE PREFERRED EMBODIMENTS

Figure 1:
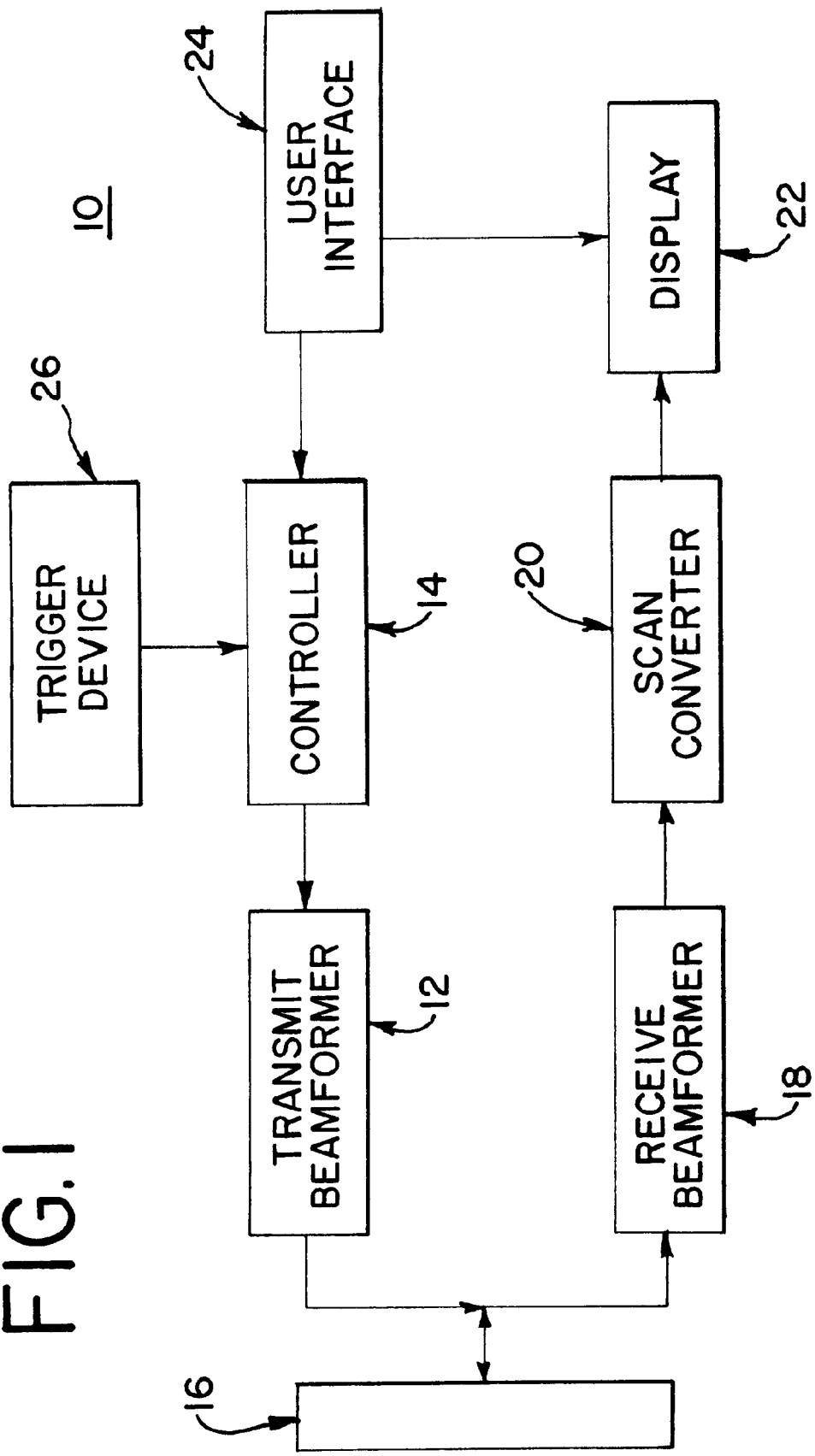
FIG. 1 is a block diagram of one embodiment of a medical diagnostic ultrasound system for delivering drugs from microspheres in response to acoustic energy.

Drug delivery through the destruction of microspheres is localized by an ultrasound system. Microspheres broadly include microbubbles, microparticles and contrast agents. A drug is placed within or otherwise attached to microspheres acoustic energy is used to destroy the microspheres in a localized area or time. For example, high acoustic power is transmitted to a localized area where the localized area is less than an area within a field of view of the system. In one embodiment, the high acoustic power is gated or triggered to a patient's heart cycle or respiratory cycle to precisely control a location of the tissue where and time when the microspheres are destroyed.

By localizing the destruction of microspheres and associated administration of the drug, a specific diseased area is exposed to a high concentration of the drug while healthy areas are exposed to lower concentrations. Furthermore, acoustic energy and the associated destruction of microspheres may damage microvasculature near or in the diseased area, possibly creating more efficient uptake of the drug or exposure of the diseased cells to the drug. By localizing delivery of a drug, lower amounts of the drug are needed in the patient or in areas not intended to be treated, lowering the risk of adverse side effects.

FIG. 1 shows one embodiment of a medical diagnostic ultrasound system for delivering drugs through the destruction of microspheres. The system 10 includes a transmit beamformer 12, a transmit beamformer controller 14, a transducer 16, a receive beamformer 18, a scan converter 20, a display 22, a user interface 24, and an optional trigger device 26. In one embodiment, the system 10 comprises a medical ultrasound system manufactured by Acuson Corporation, such as the 128XP®, Aspen™, or Sequoia® ultrasound systems. Alternatively, ultrasound systems manufactured by others may be used, including ultrasound systems using analog and/or digital processing and/or control.

The transmit beamformer 12 comprises a plurality of waveform generators, such as analog or digital waveform generators. For example, the transmit beamformer 12 comprises a beamformer disclosed in U.S. Pat. No. 5,675,554, assigned to the assignee of the present application, the disclosure of which is incorporated herein by reference. Any of various transmit beamformers for generating waveforms focused as a function of channel using delays and/or phasing to transmit acoustic energy may be used. A transmit beamformer 12 delays and/or phases the waveforms of each channel relative to other channels to focus a transmitted beam of acoustic energy along a scan line. The acoustic energy destroys microspheres containing drugs in one area while minimizing the destruction of the microspheres in another area. As used herein, drug includes various chemicals, genes, viruses, or other substances for the treatment of a patient or diseased tissues.

The controller 14 comprises an application specific integrated circuit, digital signal processor, general processor or combinations thereof for configuring and controlling the transmit beamformer 12. In one embodiment, the controller described in U.S. Pat. Nos. 5,581,517 or 5,675,554, the disclosures of which are incorporated herein by reference, are used. The controller 14 provides analog or digital signals for configuring the transmit beamformer 12 to generate the waveforms for scanning a target. In one embodiment, the controller 14 provides waveform samples or other digital data for programming the transmit beamformer 12.

The transducer 16 comprises an array of piezoelectric or microelectromechanical elements for generating acoustic energy responsive to the waveforms from the transmit beamformer. The array of elements comprises a one-dimensional or multi-dimensional transducer array. For example, a linear, curvilinear, or other one-dimensional array is provided. As another example, a 1.5D array (e.g. five elevationally spaced adjacent linear arrays), annular array or two-dimensional array of M×N elements where both M and N are greater than 1 may be provided.

In one embodiment, the transducer 16 comprises an array of elements on a catheter or an endoscope for insertion within a patient or the target. For example, the transducers disclosed in U.S. Pat. Nos. 5,345,940 and 5,325,860, the disclosures of which are incorporated herein by reference, are used. A plurality of elements connects with the plurality of transmit beamformer channels for generating an acoustic beam along one or more scan lines for destroying microspheres for drug delivery in a region of interest or minimizing the destruction of microspheres outside the region of interest.

The receive beamformer 18 comprises digital or analog components for delaying electrical signals from the transducer 16 as a function of channel or element and a summer for generating samples associated with various depths along a scan line from the delayed signals. The scan converter 20 detects the signals from the receive beamformer 18, such as detecting in a B-mode or Doppler mode (color flow mode). The scan converter 20 also converts data in a polar coordinate format into a Cartesian coordinate format for generating an ultrasound image on the display 22. The display 22 comprises a monitor or other device for displaying the ultrasound image.

The user interface 24 comprises a trackball, keyboard, mouse, microphone, or other data input device. The system 10 operates pursuant to user control provided through the user interface 24, such as receiving user input designating a region of interest. In response, the transmit beamformer 12 is configured to destroy microspheres with drugs within the region of interest and minimize the destruction of the microspheres outside the region of interest.

The trigger device 26 comprises a processor, ASIC, analog circuit or other device for generating a trigger signal. In one embodiment, the trigger device 26 generates the trigger signal in response to an input from a physiological sensor. For example, the trigger device 26 comprises an ECG trigger device for generating a trigger as a function of a heart cycle of a patient. As another example, the trigger device 26 comprises a breathing cycle device for generating a trigger signal as a function of a breathing cycle of the patient. In other embodiments, the trigger device comprises a timer for generating a trigger signal as a function of time. The trigger signal from the trigger device 26 is used for temporal control of the destruction of the microspheres with drugs.

The microspheres associated with the drug are introduced into the patient. Microspheres are provided within the patient through intravenous injection or injection into the blood stream or tissue proximate to the region to be treated. The circulatory system or other system of the patient carries the microspheres to various regions within the target, including the specific region to be treated with the drug. A region around and including the tissue to be treated is imaged with the system 10. In one embodiment, the imaging is associated with the transmission of acoustic energy adapted to minimize destruction of microspheres, such as low power B-mode imaging. Other techniques may be used to minimize the destruction of the microspheres for imaging. Once the treatment region is identified, acoustic energy adapted for the destruction of microspheres carrying the drugs is transmitted in a temporally or spatially localized process. The drug is delivered while minimizing destruction outside of the localized time or area.

FIG. 2 is a flow chart diagram of one embodiment of the operation of the system 10 for delivering drugs localized in space and/or time. In act 30, a spatial region of interest is identified. The transmit beamformer is configured as a function of the region of interest in act 32. The configuration includes settings for transmit beams adapted for the destruction of microspheres with drugs in the region of interest in act 34 and minimization of destruction of the microspheres outside the region of interest in act 36. In act 38, a trigger is provided for temporarily localizing the generation of acoustic energy for the destruction of microspheres with drugs. In act 40, acoustic energy is transmitted as a function of the configuration of the transmit beamformer 12 and any trigger. In alternative embodiments, temporary localization of the destruction of microspheres is provided without spatial localization or vice versa.

In act 30, the region of interest is identified. FIG. 3 is a graphical representation of one embodiment of an ultrasound image 50. The image 50 is oriented to image in the vicinity of the region to be treated. Low acoustic powers or other techniques are used to minimize the destruction of microspheres to generate the image 50. The user of the system 10 identifies the tissue to be treated and designates the associated region of interest 52. The region of interest 52 comprises a trapezoidal, sector, irregular or other shaped region generally including the tissue to be treated and excluding other tissue. For example, the user uses a trackball and buttons associated with the user interface 24 to designate the region of interest 52 within the image 50. In alternative embodiments, the system 10 automatically determines the region of interest 52 as a function of a threshold or other process for identifying diseased tissue from the data used to generate the image 50 or other data.

In act 32, the transmit beamformer 12 is configured by the controller 14. The transmit beamformer 12 is configured to generate waveforms for scanning a target. Microspheres within the region of interest at a particular time are destroyed, releasing drugs. The transmit beamformer 12 is also configured so that the destruction of microspheres outside the region of interest or at other times is minimized.

In one embodiment, the destruction or minimization of microspheres is controlled as a function of a frequency or power associated with the transmitted acoustic energy. Some microspheres are more likely destroyed at particular frequencies or frequency bands and less likely destroyed at other frequencies. Higher power acoustic energy is also more likely to destroy microspheres than low power acoustic energy. Either one or both of frequency and power may be used to destroy and minimize destruction of microspheres carrying drugs.

A high acoustic energy is transmitted along scan lines within the region of interest. For example, acoustic energy above a certain power level associated with the destruction of microspheres are transmitted along scan lines within the region of interest. In one embodiment, the power level is limited at a maximum level as a function of the mechanical index, other values required by regulatory agencies or the safety of the patient. Acoustic energy transmitted on scan lines outside of the region of interest is provided at a lower power. For example, the power outside the region of interest is minimized. Transmitted power is kept below a threshold power associated with the destruction of microspheres but high enough to distinguish from noise. The maximum and minimum powers discussed may be experimentally determined as a function of the microspheres. If the destruction of the microspheres is minimized outside the region of interest, some microspheres may be destroyed even with low power transmission. Likewise, not all microspheres may be destroyed in the region of interest in response to high power acoustic energy or transmit beams adapted for the destruction of microspheres.

The frequency associated with transmitted acoustic energy is selected to destroy microspheres within the region of interest. The destruction of the microspheres is minimized outside the region of interest as a function of frequency. Frequencies associated with the destruction of the microspheres may be experimentally determined. The difference between the frequencies used inside or outside of the region of interest is preferably within the bandwidth of the system 10, including the transducer 16.

For spatial localization, the beam width associated with acoustic energy for destroying microspheres is determined to minimize the destruction of microspheres outside of the region of interest. For example, in conventional color Doppler mode imaging, acoustic energy is transmitted along scan lines along the edge of the region of interest. Because of the beam width, microspheres some distance outside of the designated region of interest may be destroyed. With high acoustic powers and a fragile microspheres, this distance may be appreciable. By accounting for the beam width of the transmitted acoustic energy, the destruction of microspheres are localized. Destructive acoustic energy is transmitted along scan lines spaced away from the edge of the region of interest. The destruction of microspheres adjacent to but not within the region of interest is minimized while microspheres within the region of interest is destroyed.

In one embodiment, the focuses of the transmitted beams are changed to destroy microspheres within the region of interest and minimize destruction of the microspheres outside of the region of interest. For example, acoustic energy is distributed along scan lines within the region of interest as a function of multiple point focuses along the same scan lines. Like the line focus, the deeper distribution of high power acoustic energy or energy adapted for the destruction of microspheres throughout the region of interest provides more destruction. For regions outside the region of interest, a single point focus is used.

Alternatively, a distributed multiple point or line focus is used along scan lines outside the region of interest to provide signal-to-noise resolution along a greater depth without a peak of energy sufficient to destroy microspheres. For the smaller region of interest, a shorter line, or more confined multiple point or a single point focus, is provided for destroying microspheres.

As yet another example or as an additional focus control, the depths of the focal points are set different for scan lines within the region of interest than for outside the region of interest. For example, focal points for transmissions along scan lines within the region of interest are within the region of interest. The energy level is set such that depths outside the region are associated with a low power to minimize destruction. For scan lines outside the region of interest, the focal points are closer to or further away from the transducer in the focal points within the region of interest. By setting the focal point close to the transducer or spaced further away from the transducer, the acoustic energy and any characteristics adapted for destruction of the microspheres are minimized along a greater extent of the scan line. For example, less power is provided along a greater extent of the scan line.

In another embodiment, transmitted energy is adapted for destroying and minimizing the destruction of microspheres within and outside, respectively, the region of interest as a function of elevational focus. For example, a multidimensional transducer array is used for providing a more narrow elevational focus for acoustic energy transmitted along scan lines within the region of interest. A more narrow elevation focus provides a greater concentration of energy, more likely to destroy microspheres with drugs within the region of interest. A broader elevation focus is used for transmitting acoustic energy on scan lines outside the region of interest. The broader elevational focus minimizes the destruction of microspheres by reducing the power of the acoustic energy at any particular location along the scan line.

In another embodiment, acoustic energy is adapted to destroy or minimize destruction of the microspheres with drugs as a function of the apodization of the transmit aperture. An apodization or relative amplitude of each waveform as a function of transmit channel is selected to distribute energy such that a peak energy is lower than the energy associated with the destruction of microspheres. For energy transmitted into the region of interest, the apodization is set such that the energy exceeds the threshold of destruction in the region of interest. For example, destruction of microspheres is maximized and localized by transmitting with a low F#. The F# is determined by dividing the focal distance by the width of the transmit aperture.

In another embodiment, acoustic energy is generated by a sparse array, such as associated with shorting adjacent elements together or connecting the channels of the transmit beamformer 12 to spaced apart elements (e.g. every other element). Optimized apodizations may reduce the near field destruction of microspheres. A full aperture is used for destroying microspheres within the region of interest. Alternatively, optimized apodization reduces the near field destruction of microspheres and destroys microspheres outside and within, respectively, the region of interest for scan lines passing through the region of interest.

In another embodiment to further destroy microspheres in the region of interest, the line density is increased for scanning within the region of interest. The line density within the region is set such that a threshold energy level is exceeded throughout the entire region.

In another adaptation, the pulse repetition frequency of transmissions is increased for transmissions along scan lines within the region of interest. A higher pulse repetition frequency generates more power in the region of interest, destroying more microspheres. In one embodiment, a new transmit high pulse is fired through the region of interest before echoes have returned from all the depths of interest within the image or along the scan line. Given this high pulse repetition frequency, the ultrasound system 10 does not receive and process responsive echoes. A higher pulse repetition frequency may be used periodically so that images may be generated. U.S. Pat. No. 6,340,348 (Ser. No. 09/348, 246, filed Jul. 2, 1999) disclosure of which is herein incorporated by reference, discloses various techniques for using high pulse repetition frequencies for destroying microspheres. In an alternative embodiment, the pulse repetition frequency is increased but set low enough that responsive echoes may be received without interference from other transmissions. Any loss of correlation due to the destruction of microspheres is used to determine that microspheres are being destroyed.

Single ones or a plurality of the techniques discussed above for minimizing destruction of microspheres outside of the region of interest and maximizing the destruction of microspheres in the region of interest may be used. For example, high power transmissions with multiple focal points within the region of interest are used with low power transmission and single focal points along scan lines outside the region of interest. For areas outside of the region of interest along scan lines through the region of interest, apodization control may be used in combination with the above sequence. Other combinations may be provided. Other techniques for minimizing the destruction of microspheres outside the region of interest and maximizing the destruction of microspheres within the region of interest may be used. In yet other embodiments, the destruction of microspheres is minimized for the entire image region in general, and transmissions for the destruction of microspheres with drugs within the region of interest are continuously or periodically performed in addition.

A trigger signal is provided in act 38 for triggering the transmissions in act 40. In one embodiment, transmissions of acoustic energy associated with the destruction of microspheres is triggered, and transmissions of acoustic energy associated with minimizing the destruction of microspheres whether inside or outside the region of interest are performed substantially continuously. Alternatively, all transmissions or transmissions associated with minimization of destruction are responsive to the trigger signal.

In one example, the heart cycle is used for generating the trigger. The user of the system 10 identifies a time or time window within the cardiac cycle for the application of the drug through destruction of the microspheres. The trigger signal designates one or more of various portions of the heart cycle. For example, the trigger signal is set to identify end diastole for myocardial therapy.

In response to the trigger signal, the acoustic energy for destroying microspheres is transmitted. Acoustic energy adapted for the destruction of microspheres is transmitted along each scan line once or a plurality of times in response to each trigger. In alternative embodiments, one or more triggers are provided during a subset of every heart cycle, such as once every multiple of an integer number of heart cycles.

In yet another embodiment, the trigger signal is generated in response to the user's manual control. For example, the user presses a button or increases the transmit power. In another embodiment, the breathing cycle is monitored for generating the trigger. A trigger is generated at a particular time or time period within the breathing cycle.

Multiple trigger sources may be used, such as transmitting acoustic energy adapted for the destruction of microspheres in response to a heart cycle triggered only during a given portion of the breathing cycle. Other combinations may be provided. In another embodiment, the breathing cycle trigger indicates a time or time periods when acoustic energy adapted for the destruction of microspheres ceases. For example, if a patient takes a deep breath, high power transmissions are ceased to avoid destroying microspheres with drugs outside the region of interest or within adjacent healthy tissue.

In one embodiment, a trigger lock prevents destructive transmissions where the transducer or patient has moved. Continuous or triggered transmissions are ceased where the features or speckle pattern of the current or recent image or images do not match a reference feature or speckle pattern. For example, a correlation, such as a cross-correlation or minimum sum of absolute differences, or the region of interest indicates a sufficient match or relative movement.

In one embodiment, temporal localization in response to the triggers discussed above is used without spatial localization. In other embodiments, spatial localization without temporal localization is used. In yet other embodiments, both spatial and temporal localization are provided.

In one embodiment, delivery of drugs to a localized area is implemented using a high power color Doppler mode. The system 10 is configured to operate in a color flow mode, such as associated with Doppler processing. The user designates a color box region or region associated with Doppler imaging. This region of interest is designated using a larger, substantially continuously generated B-mode image. Doppler processing uses multiple transmissions along each scan line within a region of interest. Initially, the color mode is operated with little or no transmit power. The user of the system 10 adjusts the transmit power for a number of cardiac cycles or a period of time. During these cardiac cycles, the increased transmit power destroys microspheres within the region of interest. The user or the system 10 then reduces or turns-off the transmit power. The number of transmit firings is controlled by varying the color Doppler flow sample count (i.e. adjusting the number of transmissions along each scan line used for estimating each Doppler parameter). The beam width of the transmissions is accounted for so that acoustic energy is not transmitted along scan lines near the edge of the region of interest or color box region. For example, a small offset is introduced as a function of the beam width.

In another implementation, the user identifies a treatment region or region of interest on a B-mode image generated using low power transmissions. A color Doppler image is overlaid on the B-mode image. Based on the user's command, the ultrasound system generates acoustic energy destructive of microspheres with drugs. For example, high power ultrasound transmissions are transmitted into the region of interest. The transmissions are performed for a particular amount of time or periodically. The system 10 then returns to transmitting acoustic energy adapted to minimize the destruction of microspheres within the imaging field of view. In one embodiment, acoustic energy is transmitted just along scan lines within the region of interest during the time for destruction of microspheres. In other embodiments, transmissions outside of the region of interest with acoustic energy adapted to minimize the destruction of microspheres are provided for continuing imaging while microspheres within the region of interest are destroyed.

In one embodiment, the transducer 16 comprises a transducer adapted for insertion into the body. The transducer 16 may be positioned closer to the diseased tissue of the treatment region. A region of interest within the field of view or the entire field of view is then used for the destruction of microspheres with drugs.

While the invention has been described above by reference to various embodiments, many changes and modifications may be made without departing from the scope of the invention. For example, different imaging modes and methods for identifying a region of interest or treatment region may be used. More than one treatment region or regions of interest may be provided. Energy modes responsive to echoes at harmonic frequencies of fundamental transmitted frequencies may be used for imaging.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. An ultrasonic method for delivering drugs with a medical diagnostic ultrasound system, the method comprising the acts of:

(a) identifying a region of interest within an image of a target;

(b) generating transmit beams of acoustic energy within and outside the region of interest where the target comprises microspheres having a drug, the transmit beams within the region of interest adapted for destruction of the microspheres and the transmit beams outside the region of interest adapted for minimizing destruction of the microspheres; and (c) minimizing acoustic energy outside the region of interest.

2. The ultrasonic method of claim 1 wherein (c) comprises, for scan lines within the region of interest, transmitting beams adapted to destroy microspheres along the scan lines that are spaced away from lateral edges of the region of interest.

3. The ultrasonic method of claim 2 wherein (c) comprises accounting for beam widths of the transmissions.

4. The ultrasonic method of claim 1 wherein (c) comprises transmitting with a higher power along scan lines within the region of interest and transmitting with a lower power along scan lines outside the region of interest.

5. The ultrasonic method of claim 4 further comprising:
(d) processing signals received in response to the low power transmissions; and
wherein (c) comprises transmitting with the higher power at a pulse to pulse interval time less than the time for acoustic energy to travel from and to the transducer at a deepest depth of the region of interest.

6. The ultrasonic method of claim 1 wherein (c) comprises controlling the apodization for transmissions along scan lines within the region of interest.

7. The ultrasonic method of claim 1 wherein (b) comprises using a low F#.

8. The ultrasonic method of claim 1 wherein (c) comprises using a sparse array of elements.

9. The ultrasonic method of claim 1 wherein (b) comprises transmitting with a line focus along scan lines within the region of interest.

10. The ultrasonic method of claim 1 wherein (b) comprises transmitting to two different focal depths within the region of interest.

11. The ultrasonic method of claim 1 further comprising:
(d) triggering (b) in response to a physiological cycle.

12. The ultrasonic method of claim 10 further comprising:
(e) transmitting along scan lines outside the region of interest independent of (d).

13. The ultrasonic method of claim 1 further comprising:
(d) transmitting from a multi-dimensional array; and
wherein (b) comprises focusing (d) in the elevation dimension.

14. The ultrasonic method of claim 1 further comprising:
(d) transmitting from one of an endoscope and catheter mounted transducer.

15. The ultrasonic method of claim 1 wherein (b) and (c) comprise transmitting acoustic energy into the region of interest at a first frequency and transmitting outside the region of interest at a second frequency.

16. The ultrasonic method of claim 15 wherein (c) comprises transmitting into the region of interest at the second frequency.

17. The ultrasonic method of claim 15 wherein the first frequency is adapted for destruction of the microspheres.

18. The ultrasonic method of claim 1 wherein (c) comprises transmitting along scan lines outside the region of interest focused at a first depth and transmitting along scan lines inside the region of interest focused at a second depth less deep than the first depth.

19. The method of claim 1 wherein (b) and (c) comprise transmitting with different line densities.

20. The method of claim 1 wherein (c) comprises transmitting over an entire image area and (b) comprises additionally transmitting in the region of interest.

21. A medical diagnostic ultrasound system for delivering drugs from microspheres, the system comprising:
a transmit beamformer; and
a beamformer controller operative to configure the transmit beamformer to transmit acoustic energy within and outside a region of interest, the acoustic energy adapted to destroy microspheres within the region of interest and minimize destruction outside the region of interest, the acoustic energy within the region of interest adapted for destruction of the microspheres and the acoustic energy outside the region of interest adapted for minimizing destruction of the microspheres.

22. The system of claim 19 further comprising:
a display operable to display an image of a target; and
a user interface operable to allow designation of the region of interest as a sub-set of the image.

23. The system of claim 19 wherein the beamformer controller is operative to configure the transmit beamformer to transmit a greater amount of acoustic energy at locations within the region of interest and a lesser amount of acoustic energy at locations outside the region of interest.

24. In an ultrasonic method for delivering drugs from microspheres with ultrasound by (a) transmitting acoustic energy into a target having microspheres with a drug, the improvement comprising:
(a1) maximizing destruction of microspheres within a region of interest of the target by the acoustic energy; and
(a2) minimizing destruction of microspheres outside the region of interest in response to the acoustic energy;
wherein (a1) comprises transmitting along scan lines spaced from edges of the region of interest as a function of beam widths.

25. The method of claim 24 wherein (a1) comprises transmitting along scan lines within the region of interest at a first power, and (a2) comprises transmitting along scan lines at a second power less than the first power.

26. The method of claim 24 wherein (a1) comprises transmitting energy along a first scan line focused to at least two depths and (a2) comprises transmitting energy along a second scan line focused to a single depth.

27. The method of claim 24 wherein (a1) and (a2) comprise transmitting into the region of interest with a sparse array aperture.

28. An ultrasonic method for delivering drugs with a medical diagnostic ultrasound system, the method comprising the acts of:
(a) transmitting acoustic energy within a target comprising microspheres with drugs; and
(b) triggering (a).

29. The method of claim 28 wherein (b) comprises triggering (a) as a function of a heart cycle.

30. The method of claim 29 wherein (a) comprises maximizing destruction of the microspheres within a region of interest of the target and minimizing destruction of microspheres outside the region of interest.

31. The method of claim 30 wherein (a) comprises transmitting a greater amount of acoustic energy for locations within the region of interest and a lesser amount of acoustic energy for locations outside the region of interest.

32. The method of claim 28 wherein (b) comprises triggering (a) as a function of a breathing cycle.

33. The method of claim 28 further comprising suppressing (b) as a function of correlation.

34. A medical diagnostic ultrasound system for delivering drugs from microspheres, the system comprising:
- a transmit beamformer operative to transmit acoustic energy adapted to destroy microspheres having a drug within a region of interest; and
- a trigger device operable to trigger transmission of the acoustic energy adapted to destroy the microspheres.

35. The system of claim 34 wherein the trigger device comprises a ECG device.

36. The system of claim 34 wherein the trigger device comprises a breathing cycle device.

37. The system of claim 34 further comprising a transmit beamformer controller operative to configure the transmit beamformer to transmit the acoustic energy, the acoustic energy adapted to destroy microspheres within the region of interest and minimize destruction outside the region of interest.

38. The system of claim 34 wherein the trigger device is operable to suspend triggering in response to a correlation.

* * * * *